(12) United States Patent
Yan et al.

(10) Patent No.: US 12,038,379 B2
(45) Date of Patent: Jul. 16, 2024

(54) SANITARY DEVICE FOR URINE GLUCOSE TEST

(71) Applicant: Taiwan RedEye Biomedical Inc., Hsinchu (TW)

(72) Inventors: Shuo-Ting Yan, Hsinchu (TW); Tsung-Jui Lin, Hsinchu (TW); Yu-Hsun Chen, Hsinchu (TW); Kuan-Wei Su, Hsinchu (TW)

(73) Assignee: Taiwan RedEye Biomedical Inc., Hsinchu (TW)

( * ) Notice: Subject to any disclaimer, the term of this patent is extended or adjusted under 35 U.S.C. 154(b) by 668 days.

(21) Appl. No.: 17/324,091

(22) Filed: May 18, 2021

(65) Prior Publication Data

US 2022/0369980 A1 Nov. 24, 2022

(51) Int. Cl.
*A61B 5/20* (2006.01)
*A61B 10/00* (2006.01)
(Continued)

(52) U.S. Cl.
CPC ......... *G01N 21/552* (2013.01); *A61B 10/007* (2013.01); *G01N 21/43* (2013.01); *G01N 33/493* (2013.01)

(58) Field of Classification Search
CPC ... A61B 5/14507; A61B 5/0075; A61B 5/207; A61B 5/6891; A61B 10/007; A61B 10/0038; G01N 21/01; G01N 21/31; G01N 21/3563; G01N 21/3577; G01N 33/4833
USPC ...................... 356/128, 432–440, 51, 39–41; 250/338.1, 339.13, 341.8; 600/473, 573, 600/584
See application file for complete search history.

(56) References Cited

U.S. PATENT DOCUMENTS 5,772,606 A * 6/1998 Ashibe ................. G01N 21/359
600/584
10,575,830 B2 * 3/2020 Attar ..................... G06T 7/0014
(Continued)

FOREIGN PATENT DOCUMENTS

CN 211554031 U 9/2020
CN 212213723 U 12/2020

OTHER PUBLICATIONS

English language Abstract of CN 212213723 U (Dec. 25, 2020).
(Continued)

*Primary Examiner* — Hoa Q Pham
(74) *Attorney, Agent, or Firm* — Hershkovitz & Associates, PLLC; Abe Hershkovitz

(57) ABSTRACT

A sanitary device for the urine glucose test includes a urine container formed on an inner wall of a main body, and a measuring module with an inner space mounted at a bottom of the urine container. Within the inner space, a lens attaches to the bottom of the urine container, a rail faces a bottom surface of the lens, and a driving module moves a light unit shooting a detection beam to a measuring surface of the lens along the rail. The measuring surface contacts urine in the urine container, and reflects the detection beam out of the bottom surface into a sensor. The sensor is electrically connected to a processor. The processor determines a urine glucose level and generates a urine glucose level data instantly from an angle of incidence of the detection beam on the measuring surface and from a beam intensity signal from the sensor.

20 Claims, 12 Drawing Sheets

(51) Int. Cl.
  *G01N 21/43*   (2006.01)
  *G01N 21/552*  (2014.01)
  *G01N 33/493*  (2006.01)

(56) References Cited

U.S. PATENT DOCUMENTS

| | | | | |
|---|---|---|---|---|
| 10,591,407 | B2* | 3/2020 | Akagawa | G01N 21/3577 |
| 11,123,049 | B2* | 9/2021 | Kramer | E03D 11/00 |
| 11,311,156 | B2* | 4/2022 | Hall | A61B 5/6891 |
| 2009/0216099 | A1* | 8/2009 | Kim | A61B 5/6887 |
| | | | | 600/509 |
| 2011/0051125 | A1* | 3/2011 | Kim | A61B 5/6887 |
| | | | | 356/440 |

OTHER PUBLICATIONS

English language Abstract of CN 211554031 U (Sep. 22, 2020).
Office Action in related Taiwanese Application No. 110115764, mailed Oct. 4, 2021.

* cited by examiner

SANITARY DEVICE FOR URINE GLUCOSE TEST

BACKGROUND OF THE INVENTION

1. Field of the Invention

The present invention relates to a sanitary device, and more particularly a sanitary device for a urine glucose test.

2. Description of the Related Art

In recent years, diabetes has become more and more prevalent. A non-invasive glucose testing method is much needed for the general public to be able to monitor glucose levels without pain.

In usual circumstances, as glucose level exceeds 180 milligrams/deciliter (mg/dL), a person may have glycosuria. When the person's kidneys would not be able to absorb all the glucose in the body, the person would therefore expel excessive glucose through urine. The excessive glucose expelled through urine is called the glycosuria. The non-invasive glucose testing method is to measure the glucose level present in the person's urine.

One of the most commonly used glucose testing methods is an enzymatic method, and more particularly a glucose oxidase method by using a test strip. The test strip however requires about 30 to 60 seconds to conduct a test, making it inefficient.

The test strip is also problematic, as its result is colorimetrically determined by human eyes for color representations of glucose levels. In other words, the test strip generates inconsistent results as people perceive colors differently. Furthermore, the test strip displays only semi-quantitative results, meaning the result of the glucose levels in the person's urine is displayed within a glucose level range rather than a precise value.

Moreover, the test strip is hard to store, as a storing condition can affect its test results qualitatively. Further, while maintaining consistent quality for the test strip is hard, a test can also be inconvenient to conduct, as sampling urine requires the subject to urinate into a cup. Therefore, a better device with a more convenient way is needed to conduct a urine glucose test.

SUMMARY OF THE INVENTION

To overcome the aforementioned difficulties, the present invention provides a sanitary device for a urine glucose test. The sanitary device for the urine glucose test is able to perform the urine glucose test and collect urine without a cup, and the sanitary device for the urine glucose test uses an optical method to stably measure glucose level in a person's urine.

The sanitary device for the urine glucose test of the present invention comprises a main body and a measuring module.

The main body has a waste container and a urine container, and the urine container is formed on an inner wall of the main body.

The measuring module is mounted at a bottom of the urine container, and has an inner space. The measuring module further includes a lens, a rail, a light unit, a sensor, a processor, and a driving module.

The lens is mounted in the inner space, and includes a measuring surface and a bottom surface. The measuring surface of the lens closely attaches to the bottom of the urine container.

The rail is mounted in the inner space, and faces the bottom surface of the lens.

The light unit is movably mounted on the rail, and shoots a detection beam at the bottom surface of the lens.

The sensor is mounted in the inner space, faces the bottom surface of the lens, and receives the detection beam shooting out of the bottom surface.

The processor is mounted in the inner space, and electrically connects the light unit and the sensor.

The driving module is mounted in the inner space, connects the light unit, and electrically connects the processor. The driving module is controlled by the processor to drive the light unit to move along the rail.

When the processor receives a starting signal, the processor controls the light unit to shoot the detection beam at the bottom surface of the lens. The detection beam reflects off the measuring surface of the lens and shoots out from the bottom surface of the lens. The sensor receives the detection beam out of the bottom surface, and a beam intensity signal is generated by the sensor based on the detection beam received.

The processor further controls the driving module to drive the light unit to move along the rail, and the processor determines whether a beam intensity of the beam intensity signal is smaller than an intensity threshold. When the beam intensity determined by the processor is smaller than the intensity threshold, a position of the light unit on the rail is detected by the processor, and a urine glucose level data is generated by the processor accordingly.

The sanitary device for the urine glucose test of the present invention uses the detection beam to measure a urine glucose level, obtaining the urine glucose level and generating the urine glucose level data much faster than a current paper-based sensor.

DETAILED DESCRIPTION OF THE INVENTION

Figure 1:
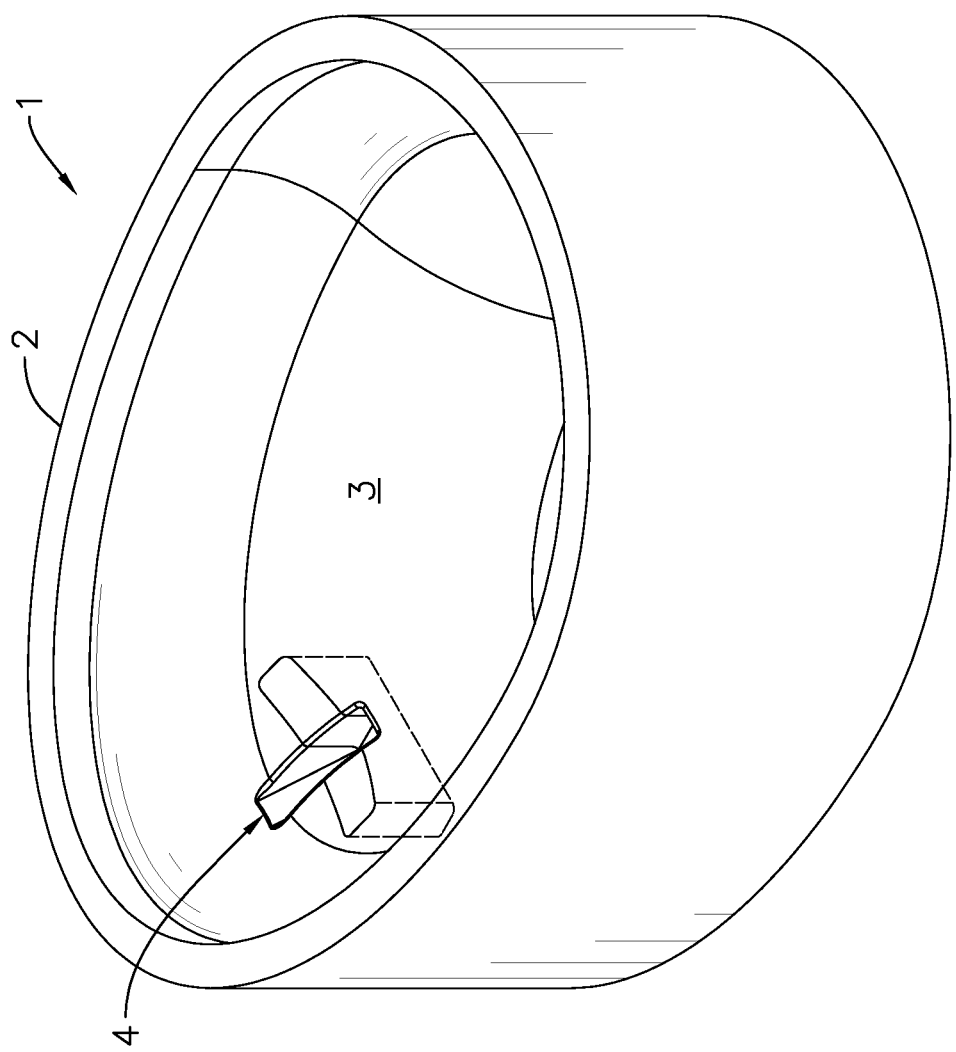
FIG. 1 is a perspective view of a sanitary device for a urine glucose test of the present invention.
Figure 2:
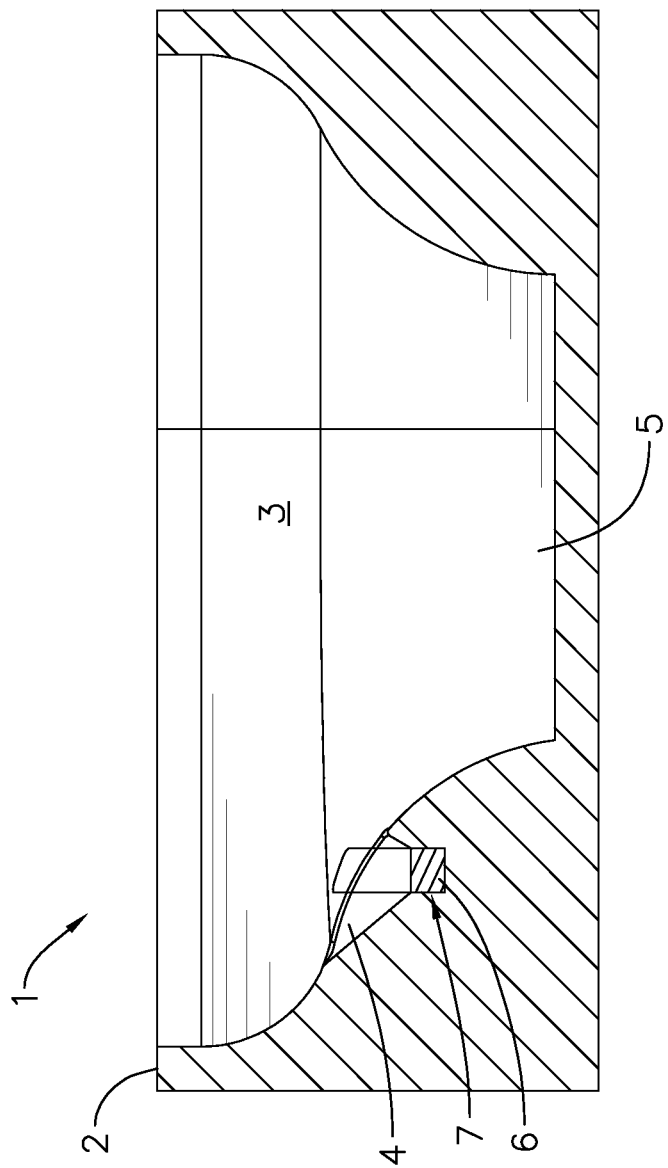
FIG. 2 is a cross-sectional view of the sanitary device for the urine glucose test of the present invention.

With reference to FIGS. 1 and 2, a sanitary device for a urine glucose test 1 of the present invention has a main body 2. The main body 2 includes a waste container 5 and a urine container 4. In FIGS. 1 and 2, in an embodiment of the sanitary device 1 of the present invention, the main body 2 is a sitting toilet. When the main body 2 is flushed, the urine container 4 is cleansed.

Figure 3:
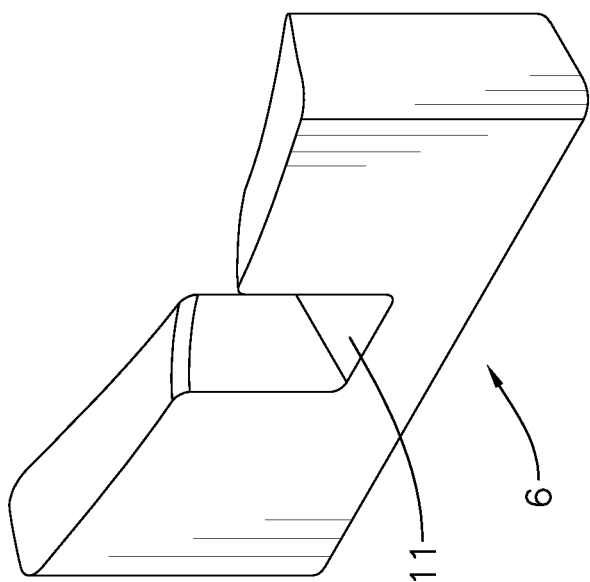
FIG. 3 is a perspective view of a measuring module of the sanitary device for the urine glucose test of the present invention.
Figure 4:
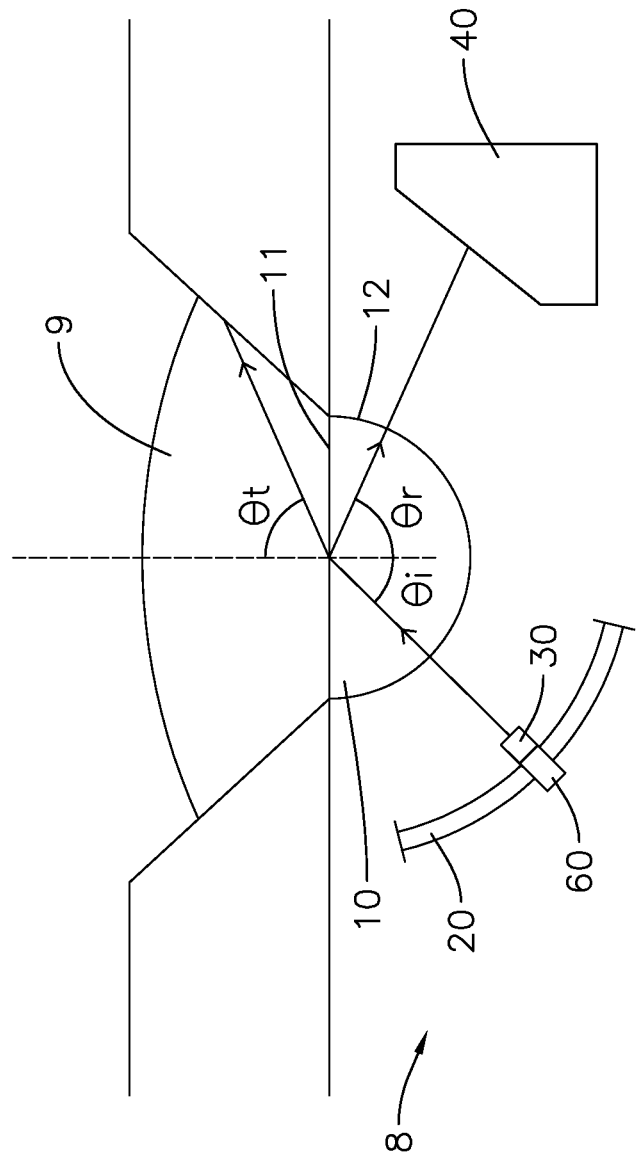
FIG. 4 is a first measuring perspective view of the measuring module of the sanitary device for the urine glucose test of the present invention.

With reference to FIGS. 3 and 4, the urine container 4 is formed on an inner wall 3 of the main body 2 for collecting urine 9. A measuring module 6 is mounted on a bottom 7 of the urine container 4. The measuring module 6 also has an inner space 8, wherein inside the inner space 8 the measuring module 6 includes a lens 10, a rail 20, a light unit 30, a sensor 40, a processor 50, and a driving module 60. In the embodiment of the present invention, the driving module 60 is a stepper motor.

The lens 10 is mounted in the inner space 8 and the lens 10 includes a measuring surface 11 and a bottom surface 12. The measuring surface 11 closely attaches to the bottom 7 of the urine container 4, and the measuring surface 11 and the inner wall 3 are closely sealed, preventing any of the urine 9 from entering the inner space 8.

The rail 20 is mounted in the inner space 8, and the rail 20 surrounds and faces the bottom surface 12 of the lens 10. The light unit 30 is movably mounted on the rail 20 in the inner space 8, and the light unit 30 shoots a detection beam from along the rail 20 at the bottom surface 12 of the lens 10. The sensor 40 is mounted in the inner space 8, and the sensor 40 faces the bottom surface 12 of the lens 10, receiving the detection beam shooting out of the bottom surface 12.

In a better embodiment of the present invention, the bottom surface 12 of the lens 10 is curved. The curved bottom surface 12 faces both the light unit 30 and the sensor 40. In the better embodiment of the present invention, the rail 20 shares a same curvature of the bottom surface 12. As a result, the detection beam moving along the rail 20 is able to maintain perpendicular angles with the curved bottom surface 12 as the detection beam enters the bottom surface 12.

Since the detection beam enters the bottom surface 12 perpendicularly, the detection beam enters the lens 10 without any angle changes. This result is an application of Snell's Law, and Snell's Law will be discussed in detail in later parts. After the detection beam enters the lens 10 perpendicularly, a refraction and a reflection would occur at a place where medium changes, or in other words, a refraction and a reflection would occur between the measuring surface 11 of the bottom 7 of the urine container 4 and the urine 9. The detection beam refracts because of medium changes from the lens 10 to the urine 9, and the detection beam reflects because a vector of the detection beam perpendicular to the measuring surface 11 changes direction. By drawing a normal line perpendicular to the measuring surface 11, when the detection beam enters a new medium, an angle of incidence $\theta_i$, an angle of reflection $\theta_r$, and an angle of refraction $\theta_t$ are created with respect to the normal line. A relationship between the angle of incidence $\theta_i$, the angle of reflection $\theta_r$, and the angle of refraction $\theta_t$, and a relationship between how much of the detection beam refracts and reflects will be discussed in detail in later parts.

The processor 50 is mounted in the inner space 8 and is electrically connected to the light unit 30 and the sensor 40. The driving module 60 is also mounted in the inner space 8 and is both connected to the light unit 30 and electrically connected to the processor 50. The processor 50 controls the driving module 60 to drive the light unit 30 to move along the rail 20.

More particularly, when the processor 50 receives a starting signal, the processor 50 controls the light unit 30 to shoot the detection beam into the bottom surface 12 of the lens 10. According to a position of the light unit 30 on the rail 20, or in other words according to an amount of how much the driving module 60 moves the light unit 30, the processor 50 is able to calculate the angle of incidence $\theta_1$ of the detection beam of the light unit 30 on the measuring surface 11. The processor 50 then analyzes a urine glucose level and generates a urine glucose level data within 3 seconds from the urine 9 based on the angle of incidence $\theta_1$ of the detection beam and based on a beam intensity of a beam intensity signal measured from the sensor 40. The present invention is able to instantly analyze the urine glucose level and generate the urine glucose level data because an optical glucose level detection method is able to provide analytical data regarding the urine glucose level in an instance as the detection beam passes and reflects from the urine 9.

Figure 5:
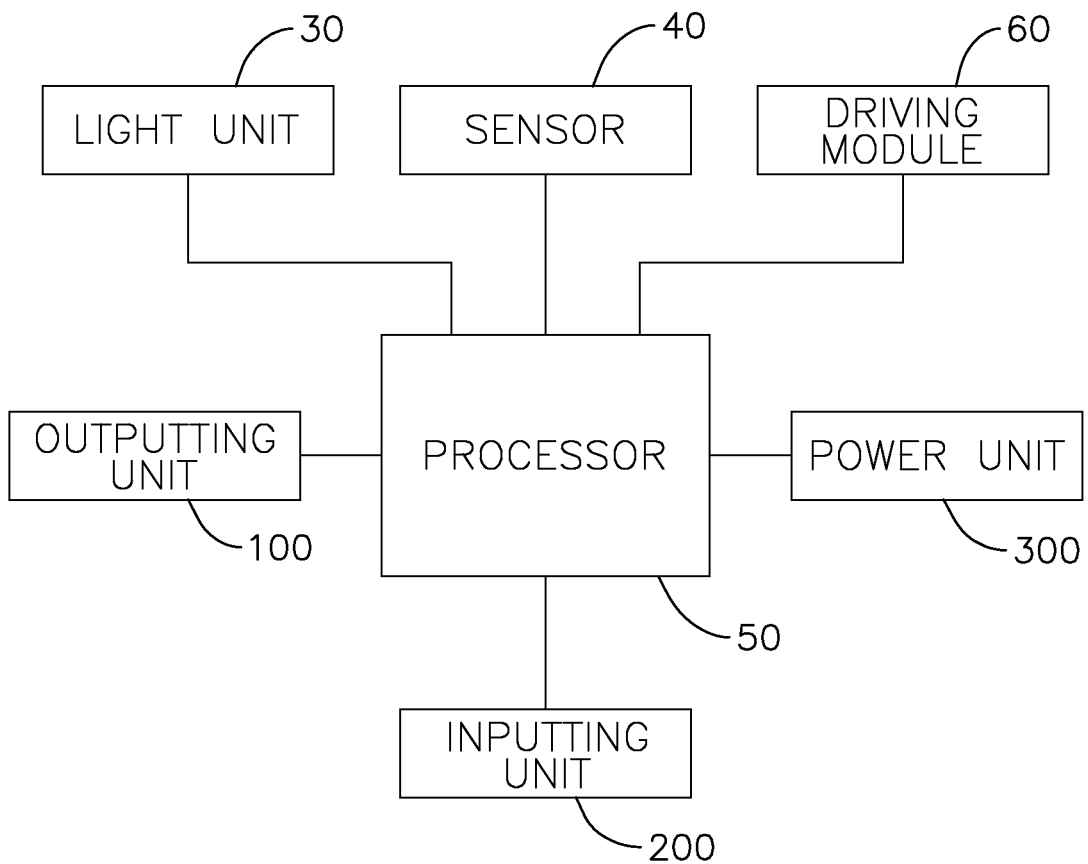
FIG. 5 is a block diagram of the sanitary device for the urine glucose test of the present invention.

With reference also to FIG. 5, in the preferred embodiment of the present invention, the processor 50 is electrically connected to an outputting unit 100, an inputting unit 200, and a power unit 300 on the main body 2 respectively.

The processor 50 further determines whether the urine glucose level data is greater than a warning level. When the urine glucose level data is greater than the warning level, the processor 50 generates a warning message, for warning a user to be more cautious about glucose levels in the blood. The processor 50 then controls the outputting unit 100 to output the warning message. In the preferred embodiment of the present invention, the outputting unit 100 is a monitor, wherein the monitor displays the warning message. Alternatively, the outputting unit 100 can also be a buzzer, wherein the buzzer makes sounds to convey the warning message.

The inputting unit 200 is responsible for generating the starting signal. Once the starting signal is generated by the inputting unit 200, the processor 50 receives the starting signal and starts working. Furthermore, the power unit 300 is responsible for supplying power in the form of electricity to the processor 50.

Before detailing how the sanitary device for the urine glucose test 1 works, a technical background of the present invention is first provided as below, describing how a light travels between two media.

Figure 6:
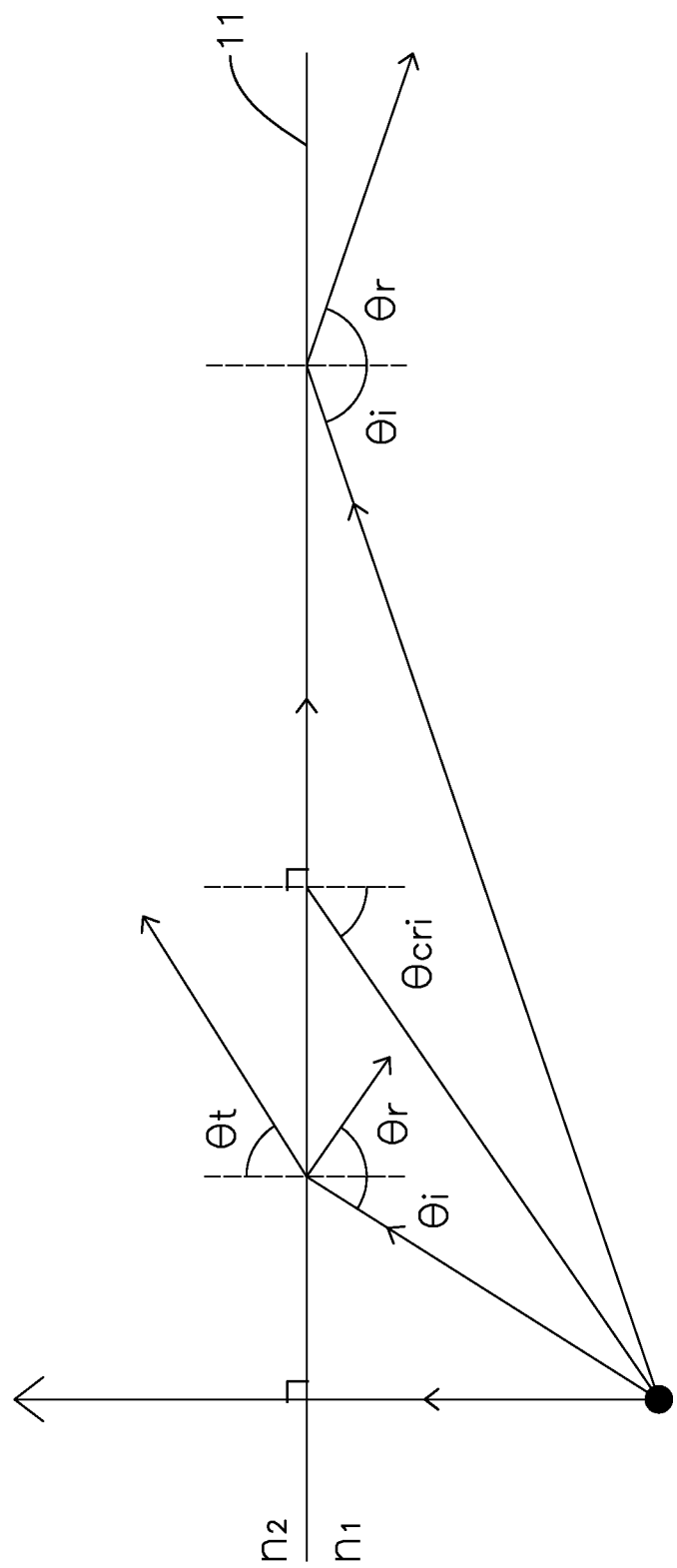
FIG. 6 is a perspective view of a total internal reflection for a beam.

With reference also to FIG. 6, let a surface between a medium one and a medium two be a flat plane. According to Snell's Law, as a light enters from one medium to another, the angle of incidence $\theta_1$, the angle of refraction $\theta_r$, a first index of refraction $n_1$, and a second index of refraction $n_2$ are related as:

$$n_1 * \sin(\theta_i) = n_2 * \sin(\theta_t),$$

wherein when $n_1 > n_2$ and the angle of incidence $\theta_i$ is at a critical angle $\theta_{cri}$, the above equation can be written as:

$$\sin(\theta_{cri}) * \frac{n_1}{n_2} = \sin(\theta_t) = 1$$

$$\theta_t = \frac{\pi}{2}.$$

In order to have $\sin(\theta_t)=1$ as shown above, the angle of refraction $\theta_t$ must be $$\frac{\pi}{2}$$

radians or 90 degrees, meaning when a light has the angle of incidence $\theta_i$ at a critical angle $\theta_{cri}$, the light will refract at 90 degrees and travel along the surface of the medium one and the medium two. When the light reflects, the angle of incidence $\theta_i$ and the angle of reflection $\theta_r$ should be the same under usual circumstances, yet an exception happens when the light has the angle of incidence $\theta_i$ exactly at the critical angle $\theta_{cri}$.

Fresnel equations can be used to further determine how much of the detection beam will refract and how much of the detection beam will reflect. According to Fresnel equations, reflectance R and transmittance T are percentages representing how much the light reflects and how much of the light refracts. In this regard, reflectance R plus transmittance T will equal 1. An incident light can be categorized as S-polarized light and P-polarized light, wherein the S-polarized light is perpendicularly polarized against the surface, and P-polarized light is parallel polarized with the surface. As the light is not particularly polarized in any way, the light is assumed to be randomly polarized by both the S-polarized light and the P-polarized light. According to the Fresnel equations, the reflectance R and the transmittance T for both the S-polarized light and the P-polarized light can be written as:

$$R_S = \left|\frac{n_1 * \cos(\theta_i) - n_2 * \cos(\theta_t)}{n_1 * \cos(\theta_i) + n_2 * \cos(\theta_t)}\right|^2,$$

$$R_P = \left|\frac{n_1 * \cos(\theta_t) - n_2 * \cos(\theta_i)}{n_1 * \cos(\theta_t) + n_2 * \cos(\theta_i)}\right|^2,$$

$$T_S = 1 - R_S, \text{ and}$$

$$T_P = 1 - R_P.$$

When $$\theta_t = \frac{\pi}{2},$$

cosine will equal zero as cos $$\left(\theta_t = \frac{\pi}{2}\right) = 0,$$

simplifying the Fresnel equations to be:

$$R_S = \left|\frac{n_1 * \cos(\theta_i) - n_2 * 0}{n_1 * \cos(\theta_i) + n_2 * 0}\right|^2 = \left|\frac{n_1 * \cos(\theta_i)}{n_1 * \cos(\theta_i)}\right|^2 = 1^2 = 1,$$

$$R_P = \left|\frac{n_1 * 0 - n_2 * \cos(\theta_i)}{n_1 * 0 + n_2 * \cos(\theta_i)}\right|^2 = \left|\frac{-n_2 * \cos(\theta_i)}{n_2 * \cos(\theta_i)}\right|^2 = 1^2 = 1,$$

$$T_S = 1 - R_S = 1 - 1 = 0, \text{ and}$$

$$T_P = 1 - R_P = 1 - 1 = 0.$$

Therefore, no matter how the incident light is polarized, both the S-polarized light and the P-polarized light will have same results. In other words, when $\theta_i = \theta_{cri}$ and $$\theta_t = \frac{\pi}{2},$$

not only will the light travel along the surface between the medium one and the medium two, but also mathematically the light is already considered as having total internal reflection, since $R_S$ and $R_P$ both equal 1.

When $\theta_i < \theta_{cri}$, the incident light will continue total internal reflection, meaning all of the light will reflect as $R_S$ and $R_P$, both stay as 1, and $T_S$ and $T_P$ both stay as 0. The angle of reflection $\theta_r$ will equal the angle of incidence $\theta_i$.

When $\theta_i = \theta_{cri}$, the incident light will travel along the surface between the medium one and the medium two. The light will reflect without the angle of reflection $\theta_r$, since when $$\theta_t = \frac{\pi}{2},$$

the angle of incidence $\theta_i$ can be mathematically viewed as $$\theta_i = \frac{\pi}{2},$$

meaning the light travels along the surface. This causes cos $$\left(\theta_i = \frac{\pi}{2}\right) = 0$$

and generates me same $R_S$ and $R_P$ results as:

$$R_S = \left|\frac{n_1 * 0 - n_2 * \cos(\theta_t)}{n_1 * 0 + n_2 * \cos(\theta_t)}\right|^2 = \left|\frac{-n_2 * \cos(\theta_t)}{n_2 * \cos(\theta_t)}\right|^2 = 1^2 = 1.$$

$$R_P = \left|\frac{n_1 * \cos(\theta_t) - n_2 * 0}{n_1 * \cos(\theta_t) + n_2 * 0}\right|^2 = \left|\frac{n_1 * \cos(\theta_t)}{n_1 * \cos(\theta_t)}\right|^2 = 1^2 = 1.$$

In another way of explaining this phenomenon, since the light travels along the surface without crossing the surface, the light travels differently than when the light reflects off the surface from medium changes. Therefore this is a special case wherein $\theta_i = \theta_{cri} \neq \theta_r$.

In the present invention, the surface discussed in FIG. 6 corresponds to the measuring surface 11, the incident light corresponds to the detection beam, the first index of refraction $n_1$ corresponds to an index of refraction of the lens 10, and the second index of refraction $n_2$ corresponds to an index of refraction of the urine 9. The index of refraction of the lens 10 is a known value, while the index of refraction of the urine 9 is an unknown value to be determined.

Figure 7:
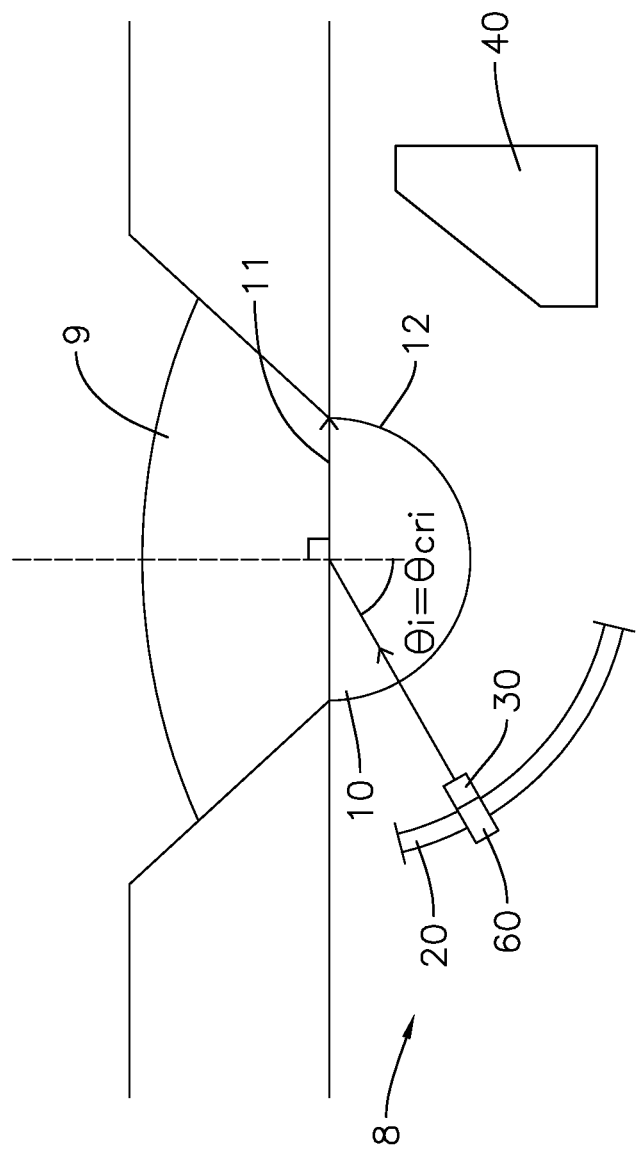
FIG. 7 is a second measuring perspective view of the measuring module of the sanitary device for the urine glucose test of the present invention.
Figure 8:
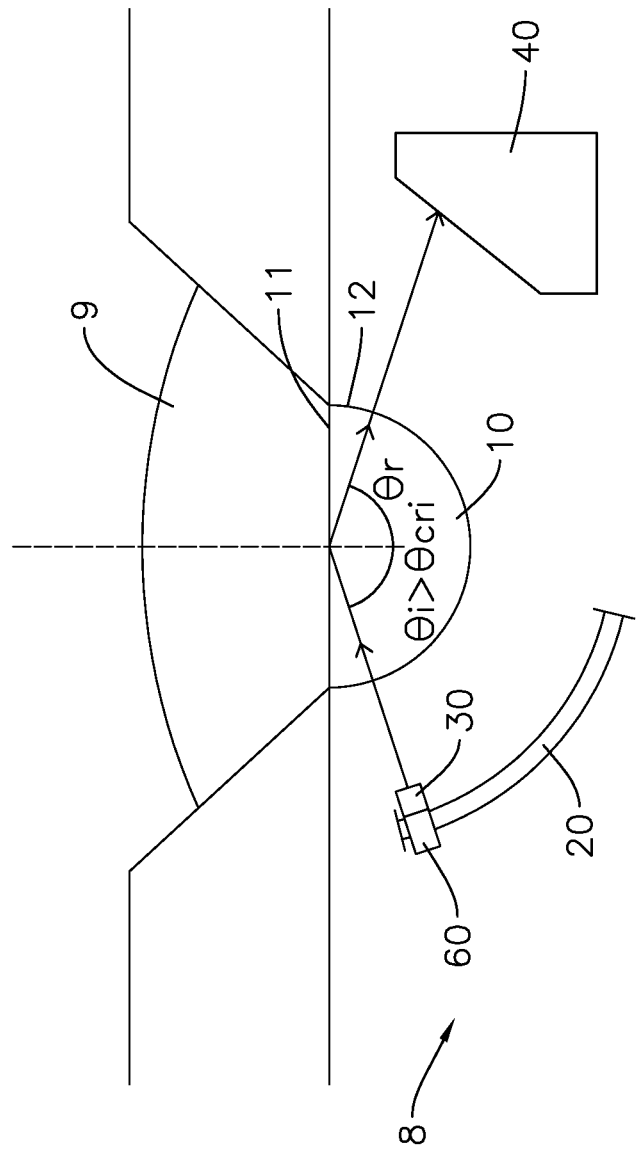
FIG. 8 is a third measuring perspective view of the measuring module of the sanitary device for the urine glucose test of the present invention.

With reference also to FIGS. 4, 7, and 8, in the better embodiment of the present invention, the aforementioned can be concluded as follows when the detector 40 detects the detection beam:
- with reference to FIG. 4, when the angle of incidence $\theta_i$>the critical angle $\theta_{cri}$, a small portion of the detection beam will reflect into the sensor 40.
- with reference to FIG. 7, when the angle of incidence $\theta_i$=the critical angle $\theta_{cri}$, all of the detection beam will travel along the measuring surface 11 due to total internal reflection, and since the sensor 40 is positioned away from the measuring surface 11, most of the detection beam will remain undetected; as a result, the beam intensity of the beam intensity signal detected by the sensor 40 will decrease to be smaller;
- with reference to FIG. 8, when the angle of incidence $\theta_i$<the critical angle $\theta_{cri}$, all of the detection beam will be reflected into the sensor 40 due to total internal reflection, and therefore, the beam intensity of the beam intensity signal detected by the sensor 40 will increase to be bigger.

Therefore, when the angle of incidence $\theta_i$ equals the critical angle $\theta_{cri}$, the beam intensity of the beam intensity signal detected by the sensor 40 at the very instance will be smaller than the beam intensity detected at any other instance when the angle of incidence $\theta_i$ equals any other degree. Conversely, when the sensor 40 detects a smallest value for the beam intensity as the angle of incidence $\theta_i$ changes, the angle of incidence $\theta_i$ at the moment will correspondingly be the critical angle $\theta_{cri}$. According to Snell's Law, the critical angle $\theta_{cri}$ can be determined as:

$$n_1 * \sin(\theta_{cri}) = n_2 * 1$$
$$\sin(\theta_{cri}) = \frac{n_2}{n_1}$$
$$\theta_{cri} = \arcsin\left(\frac{n_2}{n_1}\right).$$

The present invention is based on how the urine glucose level changes in the urine 9 can affect the index of refraction of the urine 9. More particularly, the present invention corresponds changes in the angle of incidence $\theta_i$ to the beam intensity of the beam intensity signal measured by the sensor 40 to determine the critical angle $\theta_{cri}$. Once the critical angle $\theta_{cri}$ is known, the present invention calculates the index of refraction of the urine 9 from the critical angle $\theta_{cri}$, then corresponds the index of refraction of the urine 9 to the urine glucose level, and finally generates the urine glucose level data from the processor 50.

The present invention has an intensity threshold, and the intensity threshold is adjustable. When the beam intensity of the beam intensity signal is determined by the processor 50 to be smaller than the intensity threshold, the processor 50 determines that the angle of incidence $\theta_i$ equals the critical angle $\theta_{cri}$ at a moment when the total internal reflection happens by determining the position of the light unit 30 on the rail 20 and the angle of incidence $\theta_i$ on the measuring surface 11 at the moment.

Furthermore, when the beam intensity is determined by the processor 50 to be smaller than the intensity threshold, the processor 50 further determines whether the beam intensity has a relatively small value. In other words, after the beam intensity of the beam intensity signal is determined by the processor 50 to be smaller than the intensity threshold, the processor 50 continues controlling the sensor 40 for continuous sensing while the processor 50 also continues controlling the light unit 30 moving along the rail 20. The sensing of the sensor 40 and the moving of the light unit 30 cease when the beam intensity signal sensed by the sensor 40 starts to intensify after weakening. When the beam intensity signal starts to intensify after weakening, the relatively small value will appear, and the relatively small value will be able to help the processor 50 better determine the position of the light unit 30 on the rail 20 when the critical angle $\theta_{cri}$ appears. A reason why the beam intensity signal intensifies after weakening is because when total internal reflection first happens, the beam intensity signal sensed will weaken, and when total internal reflection continues to happen after the detection beam continues to incident on the measuring surface 11 passed the critical angle $\theta_{cri}$, the beam intensity signal sensed will strengthen. Further detail about the weakening and intensifying of the beam intensity signal is covered in the abovementioned explanation regarding FIGS. 4, 7, and 8.

After the beam intensity is determined to have the relatively small value by the processor 50, the processor 50 ceases controlling the sensing of the sensor 40 and the moving of the light unit 30 because the processor 50 has obtained enough information to calculate the critical angle $\theta_{cri}$. After determining the beam intensity to be smaller than the intensity threshold and determining the beam intensity having the relatively small value, the processor 50 can firmly obtain the critical angle $\theta_{cri}$, and proceed to further calculate the urine glucose level.

Figure 9:
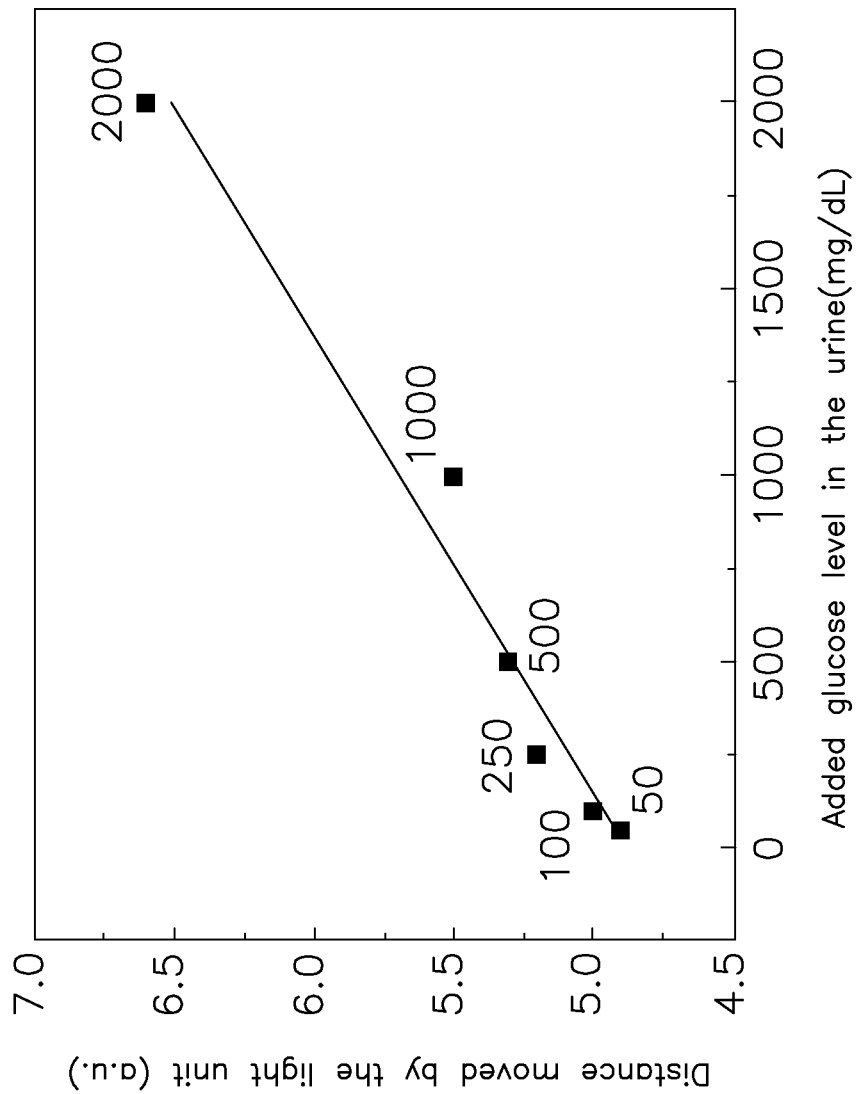
FIG. 9 is a graph showing correspondence between urine glucose level changes and moving distances of a light unit in the present invention.

With reference also to FIG. 9, an experiment data provided details a linear relationship between an added glucose level in the urine 9 and a distance moved by the light unit 30. In other words, a linear relationship exists between the urine glucose level and the distance moved by the light unit 30. In addition, linear relationships also exist between the distance moved by the light unit 30 and a changing amount of the angle of incidence $\theta_i$, as well as between the distance moved by the light unit 30 and a distance moved by the driving module 60. Therefore FIG. 9 is able to demonstrate a linear relationship between the urine glucose level and the changing amount of the angle of incidence θ. The sanitary device for the urine glucose test 1 of the present invention is able to measure the urine glucose level optically only because of this important linear relationship. The sanitary device for the urine glucose test 1 of the present invention determines the critical angle $\theta_{cri}$ from the changing amount of the angle of incidence $\theta_i$ and the beam intensity of the beam intensity signal sensed by the sensor 40, then calculates the index of refraction of the urine 9 from the critical angle $\theta_{cri}$, then linearly corresponds to the urine glucose level measured from the index of refraction of the urine 9, and finally generates the urine glucose level data from the processor 50. In the embodiment of the present invention, the distance moved by the light unit (a.u.) is measured in units such as millimeters (mm), radians (rad), degrees (°), or any other units, as the present invention allows the distance moved by the light unit (a.u.) to be measured in units of any choice. Regardless of how such distance is measured, the distance moved by the light unit 30 and the changing amount of the angle of incidence $\theta_i$ still maintain the linear relationship with each other.

In FIG. 9, the urine glucose level at 180 milligrams/deciliter (mg/dL) corresponds to the distance moved by the light unit 30 at about 5 to 5.25 a.u. When the urine glucose level exceeds 180 mg/dL, a person will start to have glucose in the urine 9. An application of the present invention satisfies a goal to measure the urine glucose level as the present invention is able to distinguish between the urine glucose levels at 50 mg/dL and at 100 mg/dL, providing better accuracy than a paper-based sensor glucose testing method.

When the urine container 4 of the present invention is flushed, remaining water in the urine container 4 will have an averaged volume. The processor 50 would take the averaged volume of the remaining water into account for calibration when calculating the urine glucose level from the urine 9. This way the urine glucose level remains accurate after the urine container 4 of the present invention is flushed.

Figure 10:
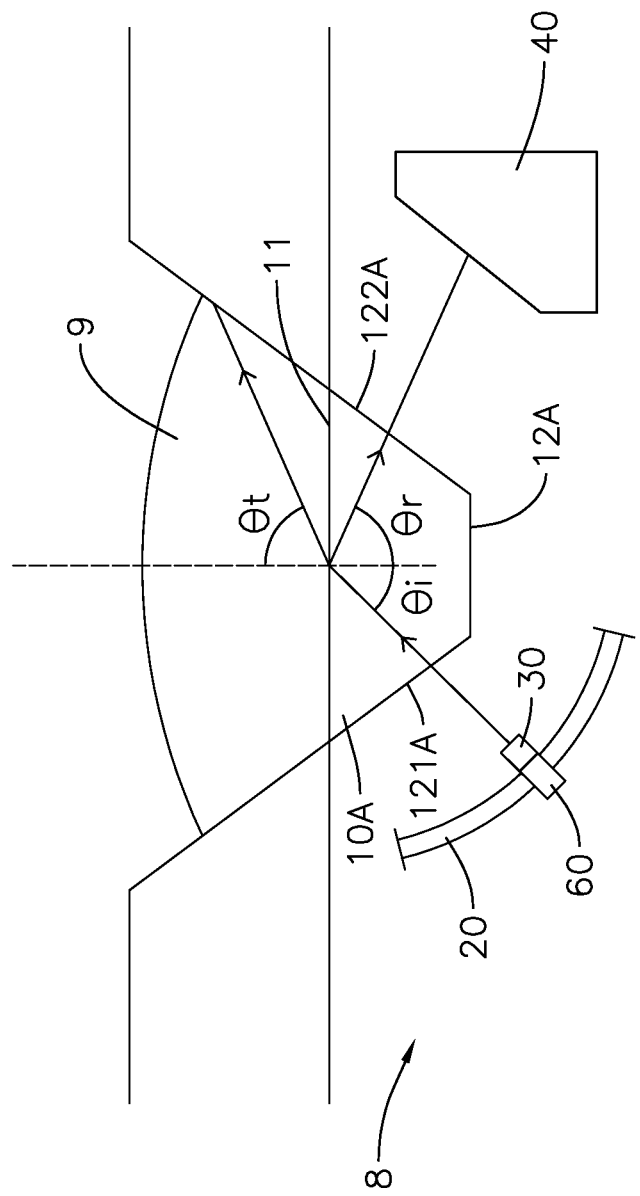
FIG. 10 is a perspective view of another embodiment of the sanitary device for the urine glucose test of the present invention.

With reference to FIG. 10, in another embodiment of the present invention, the bottom surface 12A of the lens 10A includes an entry surface 121A and an exit surface 122A. Both the entry surface 121A and the exit surface 122A are flat plane surfaces, and more particularly, the entry surface 121A faces the light unit 30, and the exit surface 122A faces the sensor 40. Namely, the detection beam is shot into the entry surface 121A of the lens 10, and is shot out from the exit surface 122A of the lens 10. Moving along the rail 20, the light unit 30 would still be able to change the angle of incidence $\theta_1$ of the detection beam for measuring the urine glucose level. When the detection beam enters from the entry surface 121A and exits the lens 10 out of the exit surface 122A, the processor 50 is able to take into account slight detection beam angle changes entering and leaving the lens 10, and eventually calculating the urine glucose level and generating the urine glucose level data in the same way.

Figure 11:
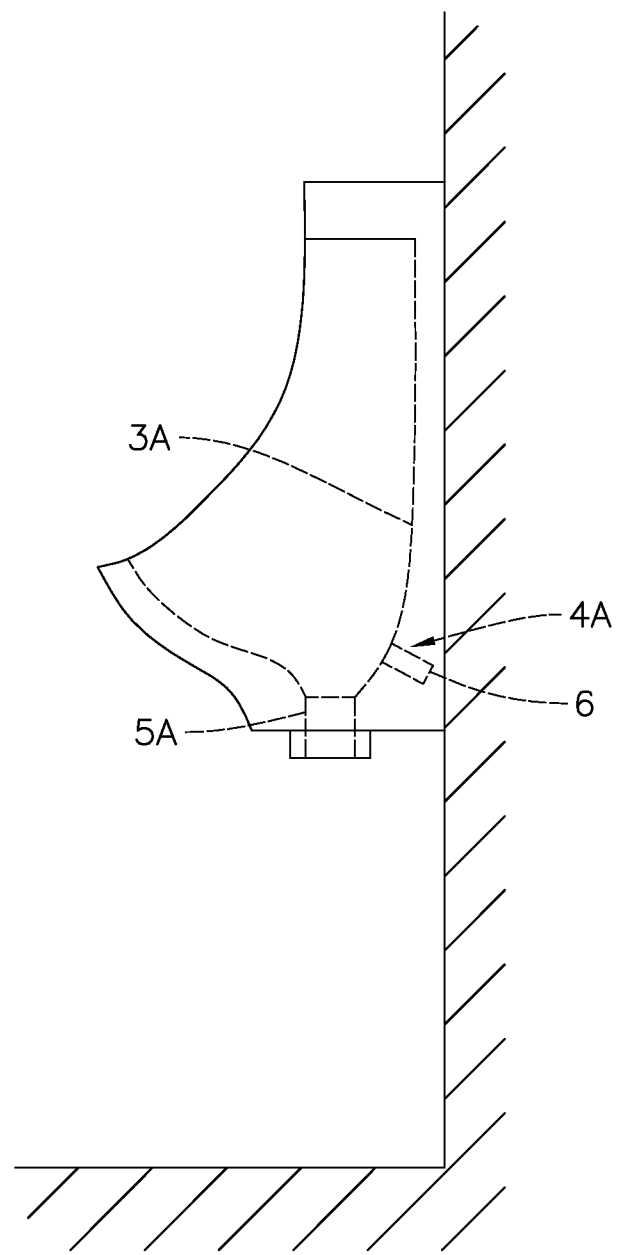
FIG. 11 is a cross-sectional perspective view of another embodiment of the sanitary device for the urine glucose test of the present invention.

With reference also to FIG. 11, in another embodiment of the present invention, the main body 2 is a urinal. The urinal also includes a waste container 5A and a urine container 4A. The urine container 4A similarly forms on an inner wall 3A of the urinal. The measuring module 6 is also similarly mounted in the urine container 4A of the inner wall 3A of the urinal. The measuring module 6 measures the urine glucose level from the urine 9 collected in the urine container 4A.

Figure 12:
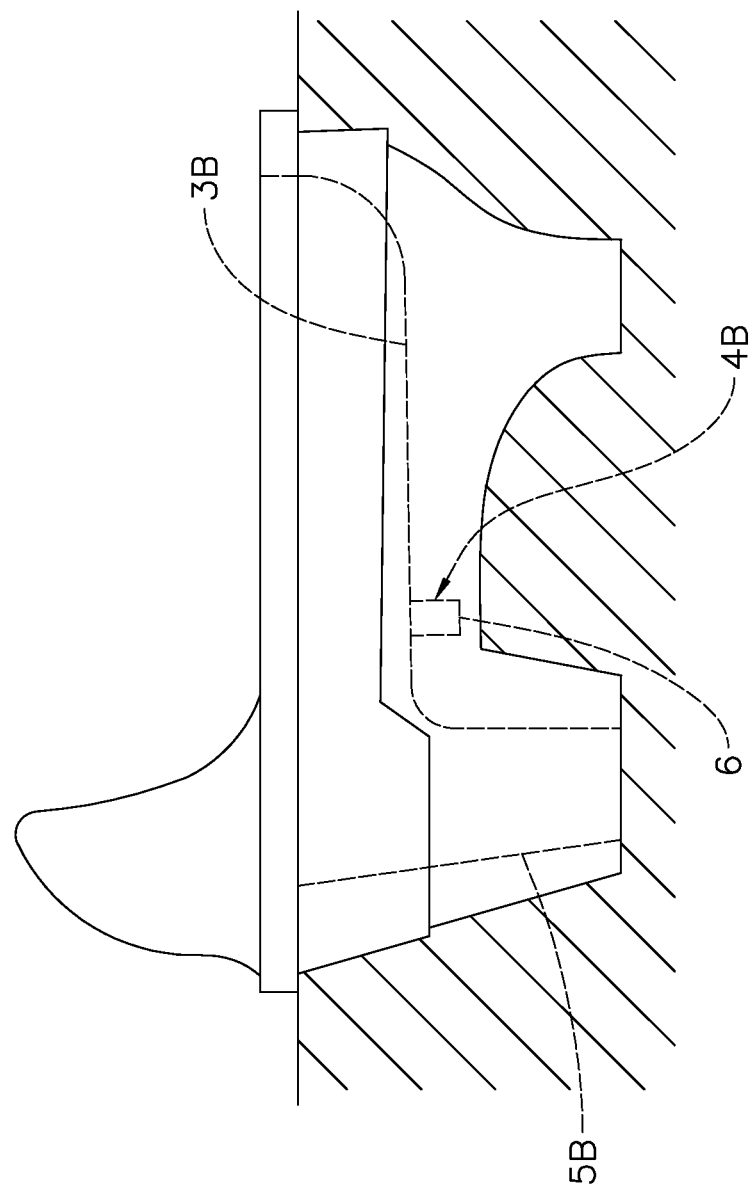
FIG. 12 is a cross-sectional perspective view of another embodiment of the sanitary device for the urine glucose test of the present invention.

With reference also to FIG. 12, in another embodiment of the present invention, the main body 2 is a squatting toilet. The squatting toilet includes a waste container 5B and a urine container 4B. The urine container 4B is formed on an inner platform 3B of the squatting toilet. The measuring module 6 is mounted in the urine container 4B of the inner platform 3B of the squatting toilet. The remaining water in the urine container 4B after flushing and remaining water on the platform 3B after flushing are summed into another averaged volume. The processor 50 would take said another averaged volume of the remaining water into account for calibration when calculating the urine glucose level from the urine 9.

In a preferred embodiment of the present invention, a volume of the urine container 4 is at least 0.5 milligram (mg), for creating a thick enough layer of the urine 9 to prevent external light sources from optically interfering with the urine glucose measurement, and as well as to provide enough sample of the urine 9 for better accuracy measuring the urine glucose level.

Furthermore, in another embodiment of the present invention, the light unit 30 can be multiple light-emitting diodes (LEDs), or a laser diode (LD), for making the detection beam well collimated. The sensor 40 can be multiple photodiodes, or a spectrometer, or a charged-coupled device sensor (CCD), or a complementary metal-oxide-semiconductor sensor (CMOS sensor). The sensor 40 can be chosen most suitably according to the wavelength of the light unit 30.

What is claimed is:

1. A sanitary device for a urine glucose test, comprising:
   a main body, having a waste container and a urine container, wherein the urine container is formed on an inner wall of the waste container of the main body;
   a measuring module, mounted on a bottom of the urine container, having an inner space, and comprising:
      a lens, mounted in the inner space, and comprising a measuring surface and a bottom surface, wherein the measuring surface of the lens closely attaches to the bottom of the urine container;
      a rail, mounted in the inner space, and facing the bottom surface of the lens;
      a light unit, movably mounted on the rail, and shooting a detection beam at the bottom surface of the lens;
      a sensor, mounted in the inner space, facing the bottom surface of the lens, and receiving the detection beam shot out of the bottom surface;
      a processor, mounted in the inner space, and electrically connecting the light unit and the sensor; and
      a driving module, mounted in the inner space, connecting the light unit, and electrically connecting the processor; wherein the driving module is controlled by the processor to drive the light unit moving along the rail; wherein:
   when the processor receives a starting signal, the light unit is controlled by the processor to shoot the detection beam at the bottom surface, and the detection beam is shot into the lens, reflected off the measuring surface of the lens, and shot out from the bottom surface into the sensor;
   the sensor generates a beam intensity signal based on the received detection beam;
   the processor controls the driving module to drive the light unit to move along the rail, and the processor determines whether a beam intensity of the beam intensity signal generated by the sensor is smaller than an intensity threshold; and
   when the beam intensity determined by the processor is smaller than the intensity threshold, a position of the light unit on the rail is detected by the processor, and the processor generates a urine glucose level data according to the position of the light unit on the rail.

2. The sanitary device for the urine glucose test as claimed in claim 1, wherein the bottom surface of the lens further comprises an entry surface and an exit surface;
   wherein both the entry surface and the exit surface are flat planes;
   wherein the detection beam is shot into the entry surface of the lens, and is shot out from the exit surface of the lens;
   wherein the entry surface faces the light unit, and the exit surface faces the sensor.

3. The sanitary device for the urine glucose test as claimed in claim 2, wherein when the beam intensity of the beam intensity signal determined by the processor is smaller than the intensity threshold, the processor further determines whether the beam intensity is a relatively small value; and
   when the beam intensity is the relatively small value, the position of the light unit on the rail is detected by the processor, and the processor generates the urine glucose level data according to the position of the light unit on the rail.

4. The sanitary device for the urine glucose test as claimed in claim 2, further comprising:
- an outputting unit, electrically connecting the processor, and mounted on the main body; wherein the processor determines whether the urine glucose level data is greater than a warning level, and when the urine glucose level data is greater than the warning level, the processor generates a warning message and controls the outputting unit to output the warning message;
- an inputting unit, electrically connecting the processor, and mounted on the main body; wherein the inputting unit generates the starting signal for the processor; and
- a power unit, electrically connecting the processor, and mounted on the main body; wherein the power unit supplies power for the processor.

5. The sanitary device for the urine glucose test as claimed in claim 4, wherein the outputting unit is a monitor or a buzzer.

6. The sanitary device for the urine glucose test as claimed in claim 2, wherein a volume of the urine container is at least 0.5 milligram (mg).

7. The sanitary device for the urine glucose test as claimed in claim 2, wherein the main body is a sitting toilet, a squatting toilet, or a urinal.

8. The sanitary device for the urine glucose test as claimed in claim 1, wherein the bottom surface of the lens is curved;
- wherein the curved bottom surface faces both the light unit and the sensor.

9. The sanitary device for the urine glucose test as claimed in claim 3, wherein when the beam intensity of the beam intensity signal determined by the processor is smaller than the intensity threshold, the processor further determines whether the beam intensity is a relatively small value; and
- when the beam intensity is the relatively small value, the position of the light unit on the rail is detected by the processor, and the processor generates the urine glucose level data according to the position of the light unit on the rail.

10. The sanitary device for the urine glucose test as claimed in claim 8, further comprising:
- an outputting unit, electrically connecting the processor, and mounted on the main body; wherein the processor determines whether the urine glucose level data is greater than a warning level, and when the urine glucose level data is greater than the warning level, the processor generates a warning message and controls the outputting unit to output the warning message;
- an inputting unit, electrically connecting the processor, and mounted on the main body; wherein the inputting unit generates the starting signal for the processor; and
- a power unit, electrically connecting the processor, and mounted on the main body; wherein the power unit supplies power for the processor.

11. The sanitary device for the urine glucose test as claimed in claim 10, wherein the outputting unit is a monitor or a buzzer.

12. The sanitary device for the urine glucose test as claimed in claim 8, wherein a volume of the urine container is at least 0.5 milligram (mg).

13. The sanitary device for the urine glucose test as claimed in claim 8, wherein the main body is a sitting toilet, a squatting toilet, or a urinal.

14. The sanitary device for the urine glucose test as claimed in claim 1, wherein when the beam intensity of the beam intensity signal determined by the processor is smaller than the intensity threshold, the processor further determines whether the beam intensity is a relatively small value; and
- when the beam intensity is the relatively small value, the position of the light unit on the rail is detected by the processor, and the processor generates the urine glucose level data according to the position of the light unit on the rail.

15. The sanitary device for the urine glucose test as claimed in claim 1, further comprising:
- an outputting unit, electrically connecting the processor, and mounted on the main body; wherein the processor determines whether the urine glucose level data is greater than a warning level, and when the urine glucose level data is greater than the warning level, the processor generates a warning message and controls the outputting unit to output the warning message;
- an inputting unit, electrically connecting the processor, and mounted on the main body; wherein the inputting unit generates the starting signal for the processor; and
- a power unit, electrically connecting the processor, and mounted on the main body; wherein the power unit supplies power for the processor.

16. The sanitary device for the urine glucose test as claimed in claim 15, wherein the outputting unit is a monitor or a buzzer.

17. The sanitary device for the urine glucose test as claimed in claim 1, wherein a volume of the urine container is at least 0.5 milligram (mg).

18. The sanitary device for the urine glucose test as claimed in claim 1, wherein the main body is a sitting toilet, a squatting toilet, or a urinal.

19. The sanitary device for the urine glucose test as claimed in claim 1, wherein the light unit is multiple light-emitting diodes (LEDs) or a laser diode.

20. The sanitary device for the urine glucose test as claimed in claim 1, wherein the sensor is multiple photodiodes, a spectrometer, a charged-couple device sensor (CCD sensor), or a complementary metal-oxide-semiconductor sensor (CMOS sensor).

* * * * *